US012679793B2

(12) United States Patent
Cotti Comettini

(10) Patent No.: US 12,679,793 B2
(45) Date of Patent: Jul. 14, 2026

(54) RECOVERY OF DIOLS FROM A MIXTURE

(71) Applicant: NOVAMONT S.P.A., Novara (IT)

(72) Inventor: Marco Cotti Comettini, Brusnengo (IT)

(73) Assignee: NOVAMONT S.P.A., Novara (IT)

( * ) Notice: Subject to any disclaimer, the term of this patent is extended or adjusted under 35 U.S.C. 154(b) by 503 days.

(21) Appl. No.: 18/548,417

(22) PCT Filed: Mar. 16, 2022

(86) PCT No.: PCT/EP2022/056849
§ 371 (c)(1),
(2) Date: Aug. 30, 2023

(87) PCT Pub. No.: WO2022/194946
PCT Pub. Date: Sep. 22, 2022

(65) Prior Publication Data
US 2024/0132429 A1 Apr. 25, 2024
US 2024/0228415 A9 Jul. 11, 2024

(30) Foreign Application Priority Data

Mar. 17, 2021 (IT) ......................... 102021000006419

(51) Int. Cl.
*C07C 29/80* (2006.01)
*C07C 29/76* (2006.01)

(52) U.S. Cl.
CPC .............. *C07C 29/80* (2013.01); *C07C 29/76* (2013.01)

(58) Field of Classification Search
CPC ........ C07C 29/80; C07C 29/76; C07C 31/207
See application file for complete search history.

(56) References Cited

U.S. PATENT DOCUMENTS

2016/0031778 A1* 2/2016 Garikipati ............... C07C 29/90
203/72
2018/0237367 A1 8/2018 Garikipati et al.

OTHER PUBLICATIONS

International Search Report and Written Opinion issued on Jul. 18, 2022 for corresponding PCT Application No. PCT/EP2022/056849.

* cited by examiner

*Primary Examiner* — Jafar F Parsa
(74) *Attorney, Agent, or Firm* — POLSINELLI PC

(57) ABSTRACT

The present invention relates to a process for purifying diols obtained by fermentation, in particular to increase their recovery during distillation operations.

20 Claims, 1 Drawing Sheet

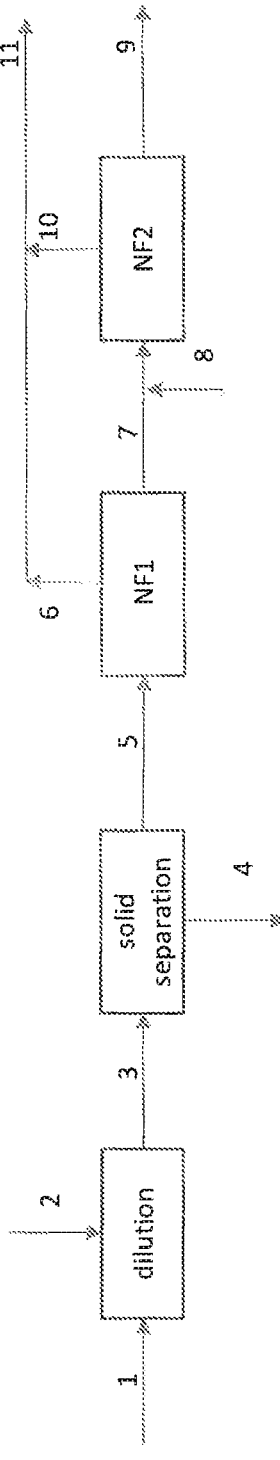
Scheme of step c) of the process according to Example 2

RECOVERY OF DIOLS FROM A MIXTURE

CROSS-REFERENCE TO RELATED APPLICATIONS

This application is a national stage application (under 35 U.S.C. § 371) of PCT/EP2022/056849, filed Mar. 16, 2022, which claims benefit of Italian Application No. 102021000006419, filed Mar. 17, 2021, which are incorporated herein by reference in their entireties.

The project leading to the invention was funded by the Bio Based Industries Joint Undertaking (JU) under grant agreement No 837866. The JU receives support from the European Union's Horizon 2020 research and innovation programme and the Bio Based Industries Consortium. The present invention relates to a process for purifying diols obtained by fermentation, in particular to increase their recovery during distillation operations.

Examples of diols are short-chain saturated aliphatic diols such as 1,3-butanediol and 1,4-butanediol.

1,3-butanediol (generally known as BG, 1,3-BG, 1,3-BDO or 1,3-butylene glycol) is a four-carbon diol with two stereoisomers: R-1,3-BDO and S-1,3-BDO. The racemic mixture is commonly used in many industrial processes, e.g. as an organic solvent for food flavouring agents or as a reagent for the production of polyurethane resins and polyesters. Due to its low toxicity and high tolerability, it is also increasingly used in the cosmetics industry in personal care products, e.g. in the formulation of hair and bath products, eye and face make-up, perfumes, personal cleansing, shaving and skin care products. Optically active 1,3-BDO is also a widely used component of antibiotics, pheromones, fragrances and insecticides.

On the other hand, 1,4-butanediol (generally known as 1,4-BDO, 1,4-BD or 1,4-butylene glycol) is widely used as a monomer for the production of various types of products such as, for example, polyesters of the diacid-diol type or as an intermediate for the synthesis of compounds such as gamma-butyrolactone and tetrahydrofuran. Polyesters comprising repeating units derived from a dicarboxylic acid and a diol are now widely used, because of their mechanical and processing properties, in all fields where thermoplastic polymer materials such as films, moulded and blown articles and fibres, are applied. It is also preferable for the polyesters thus obtained to be biodegradable, in particular according to EN 13432.

The chemical production of C2-C4 short-chain diols from fossil resources has been developed and optimised for decades. 1,3-BG is traditionally produced by a chemical process involving the hydration of acetylene to form acetaldehyde, which is then converted to 3-hydroxybutyraldehyde and reduced to form 1,3-BG.

1,4-BDO can be synthesised by various chemical processes from petrochemical raw materials: acetylene, via ethinylation with formaldehyde; butadiene, via acetylation or halogenation; propylene, via epoxidation or oxyacetylation; n-butane, via the formation of maleic anhydride and its subsequent hydrogenation by various routes.

1,3-propanediol is mainly produced by the hydration of acrolein. An alternative route involves the hydroformylation of ethylene oxide to obtain 3-hydroxypropionaldehyde, which is then hydrogenated to give 1,3-propanediol.

Due to dwindling fossil resources, fluctuating oil prices and increasing environmental problems, the production of C2-C4 diols from renewable sources by biological processes has attracted considerable interest. In fact, 1,4-BDO can be produced through fermentation processes from renewable sources such as carbohydrates, such as sugars and lignocellulosic biomass, or from synthesis gases (CO, CO2 and/or H2), directly (WO 2015/158716) or via the formation of bio-succinic acid (WO 2011/063055) and its subsequent hydrogenation or through the formation of polyhydroxyalkanoate (WO 2011/100601).

Patent application WO 2015/158716 describes a process for the production of 1,4-BDO comprising fermentation in a culture medium by a microorganism having at least one metabolic pathway for the synthesis of 1,4-BDO, in which said culture medium comprises a mixture of glucose and sucrose. Similarly, WO 2010/127319 describes a fermentation process for producing 1,3-BG from renewable sources.

1,3-propanediol can also be produced by fermentation, for example from glucose using a genetically modified strain of *E. coli*, as described in US patent 2008/176302, or from glycerol using bacteria belonging to the genus *Clostridium* (WO 2020/030775).

Processes for producing diols from both chemical and renewable sources are typically followed by purification processes to remove the unwanted impurities they contain.

Removal of these impurities is necessary to ensure that the diols can be used in, for example, cosmetics and the synthesis of diacid-diol polyesters. The higher the level of purity, the more monomers are sought after in these sectors.

In fermentation processes for the production of 1,4-BDO, such as the one described in patent application WO 2015/158716 mentioned above, the diol is synthesised by a microorganism having at least one metabolic pathway for the synthesis of 1,4-BDO from a sugar, preferably glucose and optionally one or more sugars other than glucose. The conversion of sugars to 1,4-BDO in a fermentation process is, however, typically less than 100% because, in addition to the diol, intermediates (so-called by-products) of the metabolic pathways used by the microorganisms to produce 1,4-BDO are also produced, and these may accumulate in the fermentation broth in the form of impurities.

In addition, at the end of fermentation, the organisms or cells that make up the cell biomass in the fermentation broth may be deactivated or killed, e.g. by heat, causing impurities such as residues and cellular metabolites to be released into the fermentation broth.

In diols produced by fermentation, also a number of organic compounds such as sugars, protein hydrolysates, proteins, amino acids, organic acids and yeast extracts may be found as impurities, these generally being supplied at the beginning or during fermentation, in excess of the microorganism's needs, and therefore remain in the broth at the end of fermentation. These compounds, together with the cell residues and metabolites released, can be degraded, especially during the purification process, which typically involves operations at high temperature under dehydrating conditions.

Among the by-products, the cell residues and metabolites and organic compounds mentioned above are the so-called 'heavy compounds'. Heavy compounds are defined as a mixture of compounds which are more high-boiling than the diol, i.e. compounds with a higher boiling point than the pure diol. Where the diol includes 1,4-BDO, examples of heavy compounds are 2-pyrrolidone, 1,6-hexanediol, cell residues and metabolites and organic compounds, which remain in the broth at the end of fermentation and which may have undergone a degradation process.

Processes for the purification of diols typically include distillation operations to remove these heavy compounds, which constitute the so-called "heavy fraction", characterised by high viscosity, generally from the bottom of the distillation columns. This heavy fraction is commonly disposed of in landfill or incinerated, or alternatively fed to a biodigester for biogas production, to reduce the environmental impact of the processes.

For example, patent application CN 105597351 describes a device for recovering 1,4-BDO from a fraction comprising compounds having a high boiling point (so-called "heavy fraction"). Such a device comprises a storage tank, a rising film evaporator, a falling film evaporator and a wiped film evaporator, connected in sequence. The recovered BDO is subsequently reintroduced into the purification process, while the heavy fraction is incinerated.

However, the distillation operations mentioned above may result in removal of some of the diol itself in the heavy fraction, leading to a loss of product and a decrease in plant productivity.

The heavy fraction may, in fact, contain as much as 10% to 60% by weight, typically 30 to 60% by weight of diol. Such a high diol content would not only constitute a serious loss of product, but would also make it difficult to feed the heavy fraction to a biodigester, where high diol concentrations could cause sludge inactivation and malfunction of the biodigestion plant.

In order to overcome the problems described above, it has now surprisingly been found that it is possible to recover diols from a mixture comprising these diols and compounds with a higher boiling point, making it possible to limit product losses while obtaining a heavy fraction suitable for feeding to a biodigester.

In fact, a process has been identified which allows diols to be recovered from a mixture comprising at least one diol and compounds having a boiling point higher than that of said diol, by means of one or more distillation operations for removing a fraction enriched in said compounds having a higher boiling point and subsequent dilution and filtration of said fraction. Because of the reduced diol content, the filtration retentate obtained can advantageously be fed to a biodigester for biogas production.

In addition, diols obtained as permeate can advantageously be reintroduced upstream in the purification process.

The present invention therefore relates to a process for recovering diol from a mixture comprising at least one diol and higher boiling compounds, i.e. compounds having a higher boiling point than that of the diol, said process comprising the steps of:

(a) subjecting said mixture to distillation, separating a fraction enriched in such compounds with a higher boiling point than that of the diol;

(b) diluting said enriched fraction separated in step (a) with water;

(c) subjecting the fraction diluted in step (b) to one or more filtration operations, by separating a permeate comprising the diol from a retentate comprising compounds having a boiling point higher than that of the diol.

FIG. 1 shows a diagram of process step c) according to example 2.

The fraction enriched in said compounds having a boiling point higher than that of the diol separated in step a) may also contain from 10% to 60% by weight, preferably from 20% to 50% by weight of diol, relative to the total weight of the enriched fraction.

Through the process according to the invention, it is possible to recover up to 80%, advantageously up to 90%, by weight of the diol present in the mixture comprising the diol and compounds having a higher boiling point than the diol.

The mixture according to the invention comprises at least one diol selected from: 1,2-ethanediol, 1,2-propanediol, 1,3-propanediol, 1,3-butanediol, 1,4-butanediol, 2,3-butanediol, 1,2-pentanediol, 1,3-pentanediol, 1,4-pentanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol 1,4-cyclohexanedimethanol, neopentylglycol, 2-methyl-1,3-propanediol, 3-methyl-1,5-pentanediol, 2-methyl-1,8-octanediol, 2,2-diethyl-1,3-propanediol, dianhydrosorbitol, dianhydromannitol, dianhydroiditol, cyclohexanediol, cyclohexanmethanediol, dialkylene glycols, polyalkylene glycols and mixtures thereof.

More preferably, the mixture comprises at least one linear C2-C6, preferably C2-C4, aliphatic diol.

Preferably the mixture comprises at least one diol selected from 1,2-ethanediol, 1,2-propanediol, 1,3-propanediol, 1,3-butanediol, 1,4-butanediol, 2,3-butanediol, 2-methyl-1,3-propanediol and mixtures thereof.

Even more preferably, the mixture comprises a diol selected from 1,4-BDO, 1,3-BDO and a mixture thereof. Even more preferably, the mixture comprises 1,4-BDO.

The process according to the invention is particularly advantageous because, following simple operations aimed at removing the solvent, preferably water, and any residual impurities present in the permeate, it is possible to obtain high purity diols, particularly suitable for use in polymerisation processes, in which monomers are the more sought after, the higher their level of purity.

The process according to the invention will be described in more detail below.

In step a) of the process according to the invention, a mixture comprising at least one diol and compounds having a higher boiling point than that of said diol (so-called heavy compounds) is subjected to one or more evaporation and/or distillation operations in order to separate it from solvent and/or compounds having a lower boiling point than that of said diol.

Distillation operations may be conducted by appropriately dimensioning the distillation system to effectively purify diols with different contents of impurities.

The number of distillation operations and the number of columns for each operation is not particularly limiting.

Each of the distillation operations may be conducted independently according to techniques known in the state of the art employing different types and configurations of distillation columns. For example, the distillation columns may comprise random-fill, structured-fill, flat-fill, random-fill and structured, random-fill and flat-fill, or structured-fill and flat-fill sections. Filled columns, advantageously structured fill columns, are preferred.

Each of the distillation operations can be carried out using a single column or train of columns, or through more integrated configurations that allow more than two streams to be obtained from each column, for example with side extractions of product or the insertion of vertical baffles to minimise the number of columns and ancillary equipment.

The distillation operations according to the present invention are preferably carried out by reducing or minimising exposure of the compounds to high temperatures. In fact both the products and the impurities therein may undergo thermal or chemical degradation caused by heating during distillation. Operation of the distillation columns at reduced pressure (below atmospheric pressure) or vacuum is preferred as it lowers the boiling temperature of the mixture in the distillation column and allows the distillation column to be operated at lower temperatures.

Those skilled in the art will be able to adjust the operating conditions at each step in the process to the type of column or columns used. A common vacuum system can be used with some or all of the distillation columns to achieve a reduced pressure, or each column may have its own vacuum system.

The pressure in a distillation column may be measured at the top or in the condenser, in the lower part or at the bottom or anywhere in between. The different distillation columns in the process according to the invention may operate at different pressures.

The evaporation and/or distillation operations in step a) are conducted at a temperature typically between 100 and 200° C., preferably between 120 and 170° C. The column bottom temperature generally corresponds to the boiling point of the most present diol plus 40° C., preferably 30° C., even more preferably 20° C. Preferably the applied head pressure is between 10 and 300 mbar, more preferably between 20 and 100 mbar. In this application the operating pressure of the distillation columns is understood to be measured in absolute millibars (mbar). 1 mbar corresponds to 100 Pascal.

Through step a) of the process, a fraction enriched in heavy compounds is obtained. By "enriched fraction" is meant a fraction having a heavy compounds content of more than 40% by weight, preferably more than 50% by weight, with respect to the total weight of the enriched fraction. Advantageously, it has a diol content of more than 10%, preferably more than 20%, by weight, relative to the total weight of the enriched fraction.

This fraction may have a high viscosity, typically above 500 cP.

In step b) of the process according to the invention, the fraction enriched in heavy compounds separated in step a) is diluted with water, so as to reduce its viscosity and osmotic pressure and to allow subsequent separation by filtration.

A person skilled in the art will be able to assess the most appropriate dilution based on the chosen filtration technique. For example, in the case of separation by nanofiltration, this fraction is advantageously diluted to a heavy compounds concentration of less than 10% by weight and a diol concentration of between 1 and 10% by weight, relative to the total weight of the diluted fraction.

The fraction diluted in step b) may undergo an optional solid/liquid separation step in order to remove any solid material contained therein, before undergoing filtration in step c) in the process according to the invention.

Said solid/liquid separation can be carried out by exploiting the different sizes of the particles present and comprises one or more operations chosen from pressing, squeezing, decanting, sedimentation, centrifugation, microfiltration, and any other suitable technique for solid-liquid separation and combinations thereof.

Preferably, this optional separation is conducted by microfiltration.

After optional solid/liquid separation operations the fraction obtained in step b) is subjected to filtration step c).

The filtration operations in step c) may be carried out in one or more stages and advantageously comprise ultrafiltration and/or nanofiltration. Preferably, the filtration operations comprise at least one, preferably multistage, nanofiltration operation, with at least one diafiltration stage. If more stages are present, countercurrent diafiltration may be more effective.

Depending on the characteristics of the fraction subjected to the filtration operations, those skilled in the art will be able to select the type of membrane to be used, taking into account the material of which it is made, its electrochemical properties and its porosity. On the basis of the characteristics of the selected material, a person skilled in the art will also be able to easily select the optimum pH conditions and operating pressures during each separation operation and evaluate the desirability of performing one or more diafiltration steps (i.e. dilution of the retentate by adding water and repeating the separation operation).

For example, filtration is effectively carried out using both organic membranes of natural origin (e.g. rubbers, polysaccharides) or synthetic origin (e.g. polymer membranes), and inorganic membranes, such as ceramic, metal or glass membranes. Among the organic membranes, polyamides, polyimides, polyalkylenes, polyether imides, polyarene ethers, poly(ether ketones), polycarbonates, cellulose acetate and derivatives are preferred. Specific examples of suitable organic membranes are polysulfones, aromatic polyamides, polypiperazine amide, polyethylene, polytetrafluoroethylene (PTFE), polypropylene, polyvinyl alcohol, polystyrene, polybenzimidazoles (PBI), polyphenylenes, polyphosphazenes, polyvinylidene fluoride (PVDF), polyether sulfones (PES), polyacrylonitrile (PAN), polyvinylchloride (PVC). Both isotropic (or symmetrical) and anisotropic (or asymmetrical) membranes and composite membranes are suitable. Preferably, anisotropic membranes are used.

Porous membranes (i.e. with a pore size of 1 nm to 10 μm, e.g. macroporous >50 nm, mesoporous from 2 nm to 50 nm, microporous from 1 nm to 2 nm) may be used in this process. Dense membranes (with a pore size <1 nm) may also advantageously be used, particularly after at least one preliminary membrane separation operation.

Said membranes used in step c) advantageously have an average pore size of 5 nm or less, even more advantageously an average pore size ranging from 2 nm (corresponding to a molecular cut-off or MWCO of about 1000-1200 Da) to 0.7 nm (corresponding to about 120-150 Da). Membranes may be formed in different configurations, such as flat, tubular, capillary or hollow fibre. Flat membranes can be used as they are in filter-press systems, in rotary systems or wound in spiral modules to increase the surface/volume ratio.

The filtration operations according to the invention may be carried out as batch or continuous processes; depending on the case, a filtration method in normal (perpendicular) flow regime or tangential flow regime is respectively preferred. Separation operations through a membrane in the tangential flow regime are preferred.

The nanofiltration operations are preferably carried out according to the invention using membranes made of material selected from the group consisting of: polysulfones, polypiperazine amide, polyamides, polyimides.

During the filtration operation(s) in step c), the mixture is preferably maintained at a temperature from room temperature (20° C. to 25° C.) to 50° C., more preferably 35° C. to 45° C. At the end of filtration step (c) a permeate, comprising the diol, is separated from a retentate, comprising the more high-boiling compounds, i.e. compounds with a higher boiling point than that of the diol.

The diols obtained in the permeate of step c) of the process according to the invention may advantageously undergo a purification process comprising further optional solid/liquid separation and/or concentration and/or distillation operations aimed at removing water and possible residual impurities. Such operations make it possible to obtain high purity diols, suitable for use in polymerisation processes, and to increase the overall yield of production plants.

The additional optional solid/liquid separation operations may for example be carried out by one or more of decantation, centrifugation, filtration, microfiltration, nanofiltration, ultrafiltration, ion exchange, osmosis, other suitable solid/liquid separation techniques and combinations thereof.

According to one aspect of the invention, compounds with a higher boiling point than that of the diol include compounds with low molecular weight and low rejection, which could therefore pass into the permeate of step c), thereby decreasing the purity of the diol.

In this case, the process according to the present invention advantageously comprises, after step c), an optional step d) in which the permeate is concentrated, for example by evaporation or reverse osmosis, and a subsequent step e) in which the concentrated permeate is treated by means of ion exchange, adsorption or another technique allowing the separation of impurities from the stream containing the diol. The permeate thus treated may advantageously be reintroduced upstream in the purification process and undergo further optional solid/liquid separation and/or concentration and/or distillation operations aimed at removing water and possible residual impurities. This embodiment of the invention is particularly advantageous for recovering 1,4-BDO from mixtures containing compounds having a low molecular weight and a boiling point higher than that of 1,4 BDO, such as for example 2-pyrrolidone.

The mixture comprising diols and heavy compounds may be derived from a process for purifying diols obtained from biomass, for example from previous distillation operations typically carried out to remove the solvent. The process according to the invention is therefore advantageously applied to processes for purifying diols comprising distillation operations.

The permeate obtained at the end of step c) or optional step e) may for example undergo one or more treatments with ion exchange resins, as described in patent application WO 2019/102030. These resins may be cationic or anionic exchange resins.

Cation exchange resins are generally selected from the group consisting of resins derived from strong acids (e.g. sulfonate groups) or weak acids (e.g. carboxylate groups) and preferably contain functional groups selected from the sulfonate groups. Non-limiting examples of cation exchange resins include, for example, the resin commercially available under the brand names DOWEX® 88 or DOWEX® 88 MB.

Anion exchange resins are generally selected from the group consisting of resins derived from strong bases (e.g. quaternary amine groups) or weak bases (e.g. tertiary amine groups) and preferably contain functional groups selected from quaternary amine groups. Non-limiting examples of anion exchange resins include, for example, the resin commercially available under the brand name DOWEX® 22.

The order of the passes through the cation and anion exchange resins is not particularly limiting. One or more passes through cation exchange resins may precede or succeed one or more passes through anion exchange resins. Preferably, the one or more passes through cation exchange resins precede one or more passes through anion exchange resins.

The permeate obtained at the end of step c) or optional step e) or the solution obtained after treatments with ion exchange resins or between the different passes through these resins, may undergo concentration operations by techniques known to those skilled in the art.

The concentration operations may for example be chosen from evaporation and/or reverse osmosis.

The permeate obtained at the end of step c) or optional step e) or the aqueous solution obtained after passing through the ion exchange resins or after concentration may undergo distillation operations.

According to one embodiment, the permeate obtained at the end of step c) is subjected to evaporation, ion exchange treatment and distillation.

The following examples illustrate, but are not limited to, the present invention.

EXAMPLES

Example 1

Step a)

A mixture of a biological nature comprising 80% by weight of 1,4-BDO, water and impurities derived from the production process (including 0.76% by weight of compounds having a higher boiling point than that of 1,4-BDO, relative to the weight of the mixture) was fed into a first distillation column to remove water, operated at a head pressure of about 110 mbar. The bottoms from the first column were sent to a second separation column, operated at a head pressure of about 33 mbar.

The fraction separated from the bottom of the second column was fed to a film evaporator operated at 10 mbar, resulting in a fraction enriched in heavy compounds, having a content of 70% by weight with respect to the total enriched fraction of such compounds having a higher boiling point than that of the diol and a diol content of 30% by weight with respect to the weight of the enriched fraction.

Step b)

An aliquot of the heavy compound-enriched fraction separated in step a) was diluted with water to a heavy compound concentration of 8.6% w/w relative to the total weight of the diluted fraction (weight ratio 1:8).

Step c)

The fraction diluted in step b) underwent a first filtration on paper in order to retain any solid compounds, followed by nanofiltration using a laboratory filtration module (Lab-stack™ M20), equipped with membranes (NF PET series).

Nanofiltration was carried out in batch mode, at 30 bar pressure, with recycling of the retentate into the feed tank and continuous extraction of the permeate.

The operation was conducted until a VCF of 4 was obtained, resulting in a clear permeate. Throughout the nanofiltration the BDO had a rejection between 0 and 10%.

Example 2

Using a mixture having the composition of the dilute solution prepared in step b) of example 1, a simulation of step c) of the process is performed on a spreadsheet.

After filtration with bag filters to retain any solid deposits, the diluted solution is subjected to a continuous nanofiltration process according to the scheme in FIG. 1, consisting of a first concentration step and a second diafiltration step. The first step is conducted to a VCF of 3, the second step to 3.2. The diafiltration is performed by feeding water to the retentate from the first step in a ratio of 2:1. The compositions of the inlet and outlet flows in each step (1-11) are shown in Table 1.

As can be seen from Table 1, at the end of step (c) a retentate (9) comprising 26.9% by weight of compounds with a higher boiling point than that of the diol, relative to the weight of the retentate, is obtained.

Through steps b) and c) more than 83% of the 1,4-BDO present in the enriched fraction is able to be recovered in the permeate (11), increasing recovery of the diol distilled in step a). The permeate, being a clear dilute solution of BDO, can conveniently be recycled upstream in the production process, with obvious economic advantages.

8. The process according to claim 1, wherein the filtration operations in step c) comprise ultrafiltration and/or nanofiltration.

9. The process according to claim 8, wherein the filtration operations in step c) comprise nanofiltration.

TABLE 1

| | 1<br>H | 2<br>H2O | 3<br>H dil | 4<br>S out | 5<br>L out | 6<br>P1 | 7<br>R1 | 8<br>D | 7 + 8<br>F2 | 9<br>R2 | 10<br>P2 | 11<br>P tot |
|---|---|---|---|---|---|---|---|---|---|---|---|---|
| | | | | | Flow rates (kg/h) | | | | | | | |
| $H_2O$ | — | 350 | 350 | 3.903 | 346.09 | 254. | | 263. | 355.45 | | 267.5 | 521.5 |
| BDO | 15 | — | 15 | 0.167 | | | | — | | | 3.7 | 12.6 |
| Heavy | 34.5 | — | 34.5 | 0.385 | | | | — | | | 0.5 | 0.9 |
| Solids | 0.5 | — | 0.5 | 0.495 | | | | — | | | 0.0 | 0.0 |
| Total | 50 | 350 | 400 | 4.95 | 395.05 | 263. | 131.7 | 263. | 395.1 | 123.5 | 271.6 | 535.0 |
| | | | | | Composition (%) | | | | | | | |
| $H_2O$ | — | 100.0 | | 78.8 | 87.6 | | 69.9 | 100. | 90.0 | 71.3 | 98.5 | 97.5 |
| BDO | 30.0 | — | | 3.4 | 3.8 | | 4.5 | — | 1.5 | 1.8 | 1.4 | 2.352 |
| Heavy | 69.0 | — | 8.6 | 7.8 | 8.6 | | 25.6 | — | 8.5 | 26.9 | 0.2 | 0.2 |
| Solids | 1.0 | — | 0.1 | 10.0 | 0.0 | | 0.0 | — | 0.0 | 0.0 | 0.0 | 0.0 |
| Total | 100.0 | 100.0 | 100.0 | 100.0 | 100.0 | 100. | 100.0 | 100. | 100.0 | 100.0 | 100.0 | 100.0 |

The invention claimed is:

1. A process for the recovery of diol from a mixture comprising at least one diol and higher boiling compounds, having a higher boiling point than that of the diol, said process comprising the steps of:
(a) subjecting the said mixture to distillation, separating a fraction enriched in said higher boiling compounds;
(b) diluting said enriched fraction separated in step (a) with water;
(c) subjecting the fraction diluted in step (b) to one or more filtration operations, by separating a permeate comprising the diol from a retentate comprising the higher boiling compounds.

2. The process according to claim 1, in which the mixture comprises at least one diol selected from: 1,2-ethanediol, 1,2-propanediol, 1,3-propanediol, 1,3-butanediol, 1,4-butanediol, 2,3-butanediol, 1,2-pentanediol, 1,3-pentanediol, 1,4-pentanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol 1,4-cyclohexanedimethanol, neopentylglycol, 2-methyl-1,3-propanediol, 3-methyl-1,5-pentanediol, 2-methyl-1,8-octanediol, 2,2-diethyl-1,3-propanediol, dianhydrosorbitol, dianhydromannitol, dianhydroiditol, cyclohexanediol, cyclohexanmethanediol, dialkylene glycols, polyalkylene glycols and mixtures thereof.

3. The process according to claim 2, wherein said at least one diol is a linear C2-C6 aliphatic diol.

4. The process according to claim 3, wherein said C2-C6 aliphatic diol is selected from 1,2-ethanediol, 1,2-propanediol, 1,3-propanediol, 1,3-butanediol, 1,4-butanediol, 2,3-butanediol, 2-methyl-1,3-propanediol and mixtures thereof.

5. The process according to claim 4, wherein said C2-C6 aliphatic diol is 1,3-butanediol and/or 1,4-butanediol.

6. The process according to claim 1, wherein the enriched fraction separated in step a) has a content of more than 40% by weight of compounds having a higher boiling point than that of the diol, relative to the weight of the enriched fraction.

7. The process according to claim 1, in which the enriched fraction separated in step a) has a diol content of 10% to 60% by weight relative to the total weight of the enriched fraction.

10. The process according to claim 1, wherein said filtration operations in step c) are conducted in multiple stages.

11. The process according to claim 2, wherein the enriched fraction separated in step a) has a content of more than 40% by weight of compounds having a higher boiling point than that of the diol, relative to the weight of the enriched fraction.

12. The process according to claim 3, wherein the enriched fraction separated in step a) has a content of more than 40% by weight of compounds having a higher boiling point than that of the diol, relative to the weight of the enriched fraction.

13. The process according to claim 4, wherein the enriched fraction separated in step a) has a content of more than 40% by weight of compounds having a higher boiling point than that of the diol, relative to the weight of the enriched fraction.

14. The process according to claim 5, wherein the enriched fraction separated in step a) has a content of more than 40% by weight of compounds having a higher boiling point than that of the diol, relative to the weight of the enriched fraction.

15. The process according to claim 2, in which the enriched fraction separated in step a) has a diol content of 10% to 60% by weight relative to the total weight of the enriched fraction.

16. The process according to claim 3, in which the enriched fraction separated in step a) has a diol content of 10% to 60% by weight relative to the total weight of the enriched fraction.

17. The process according to claim 4, in which the enriched fraction separated in step a) has a diol content of 10% to 60% by weight relative to the total weight of the enriched fraction.

18. The process according to claim 5, in which the enriched fraction separated in step a) has a diol content of 10% to 60% by weight relative to the total weight of the enriched fraction.

19. The process according to claim 6, in which the enriched fraction separated in step a) has a diol content of 10% to 60% by weight relative to the total weight of the enriched fraction.

20. The process according to claim 2, wherein the filtration operations in step c) comprise ultrafiltration and/or nanofiltration.

\* \* \* \* \*